(12) United States Patent
Sugimoto

(10) Patent No.: US 8,797,515 B2
(45) Date of Patent: Aug. 5, 2014

(54) DEFORMATION MEASURING APPARATUS AND DEFORMATION MEASURING METHOD

(75) Inventor: Takashi Sugimoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 17 days.

(21) Appl. No.: 13/114,238

(22) Filed: May 24, 2011

(65) Prior Publication Data

US 2011/0299064 A1 Dec. 8, 2011

(30) Foreign Application Priority Data

Jun. 4, 2010 (JP) ................. 2010-129275

(51) Int. Cl.
| | | |
|---|---|---|
| *G01L 1/24* | (2006.01) | |
| *G01B 11/24* | (2006.01) | |
| *G01B 11/30* | (2006.01) | |
| *G01B 11/02* | (2006.01) | |
| *G01B 9/02* | (2006.01) | |
| *G01B 11/16* | (2006.01) | |

(52) U.S. Cl.
CPC .......... *G01B 9/02095* (2013.01); *G01B 11/162* (2013.01)
USPC .......... 356/35.5; 356/601; 356/612; 356/502; 356/511; 356/512

(58) Field of Classification Search
CPC ................ G01B 9/02094–9/36; G01B 11/162; G01B 11/2441; G01B 11/306; G01B 11/0675; G01J 9/02
USPC .......................... 356/35.5, 450–521, 601, 612
See application file for complete search history.

(56) References Cited

U.S. PATENT DOCUMENTS

| 6,943,870 B2 * | 9/2005 | Toyooka et al. ............. 356/35.5 |
| 7,423,766 B1 * | 9/2008 | Li ................................. 356/521 |
| 2004/0179204 A1 | 9/2004 | Hizuka | |

FOREIGN PATENT DOCUMENTS

| JP | 6-94434 A | 4/1994 |
| JP | 2000-231065 A | 8/2000 |
| JP | 2004-109075 A | 4/2004 |
| WO | 2006-001712 A2 | 1/2006 |

OTHER PUBLICATIONS

KREIS, Computer Aided Evaluation of Fringe Patters, Optics and Lasers in Engineering, 1993, vol. 19, pp. 221-240.

* cited by examiner

*Primary Examiner* — Gregory J Toatley
*Assistant Examiner* — Hina F Ayub
(74) *Attorney, Agent, or Firm* — Canon USA, Inc. IP Division

(57) ABSTRACT

An apparatus and a method capable of measuring large deformation with a high accuracy and dynamically, using speckle interference, utilizes an optical path where one laser beam out of two laser beams becomes non-collimated light and a plane parallel transparent plate, and can form carrier fringes. More specifically, the transparent plate is arranged on the optical path where the non-collimated light is formed, or is removed from the optical path, or a refractive index, or a thickness of the transparent plate arranged on the optical path, or a tilt angle relative to an optical axis is changed. The phase analysis can be performed from fringe images corresponding to the deformation, by performing repetitively the above-described processing and acquisition of the speckle interference pattern.

6 Claims, 9 Drawing Sheets

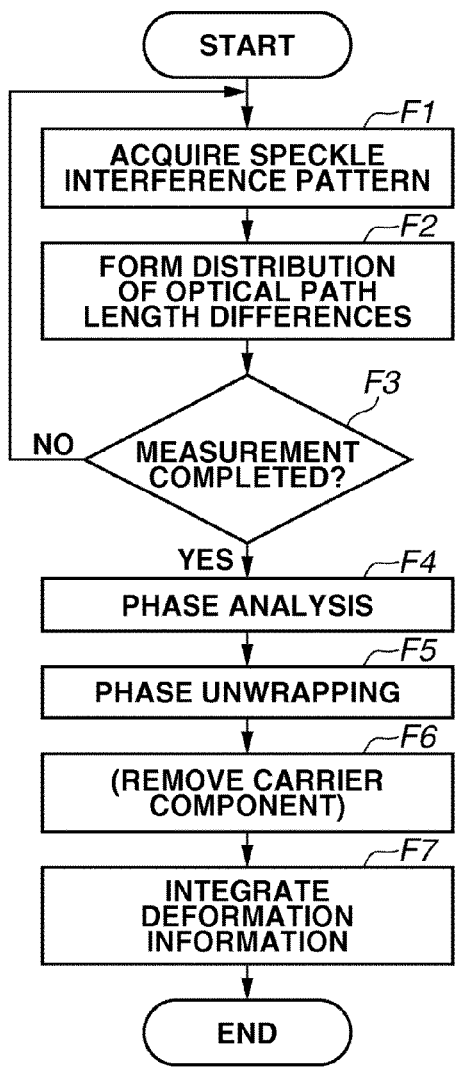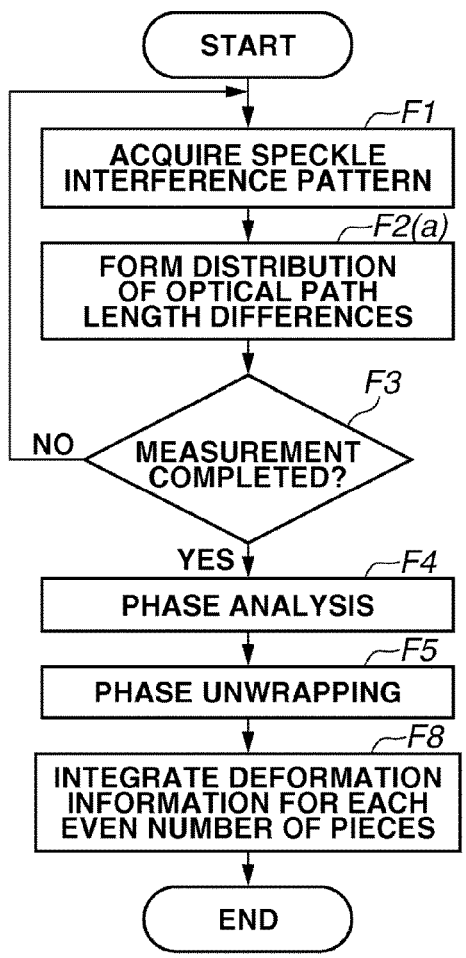

FIG.6A
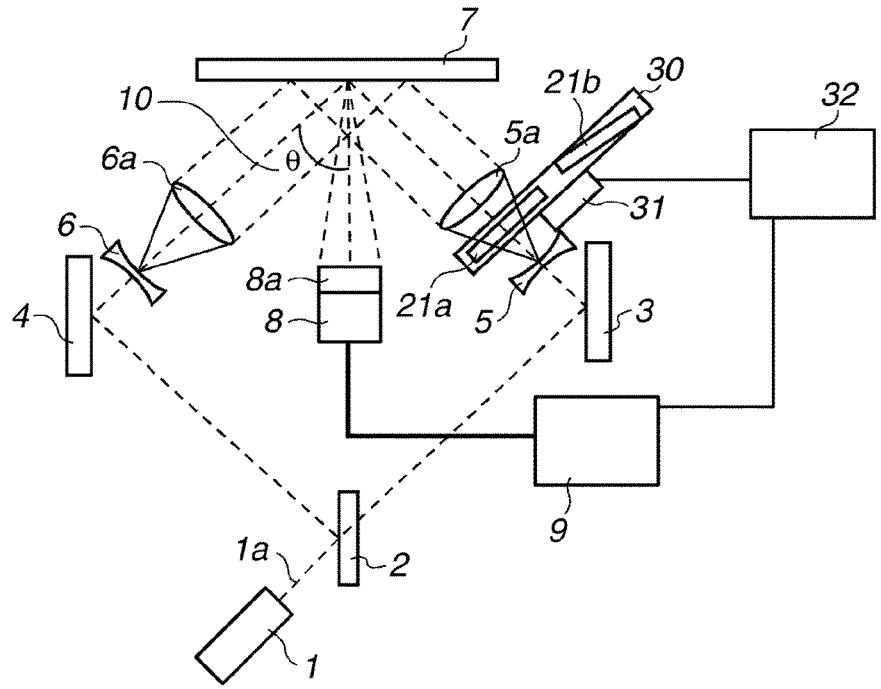
FIG.6B
FIG.6C
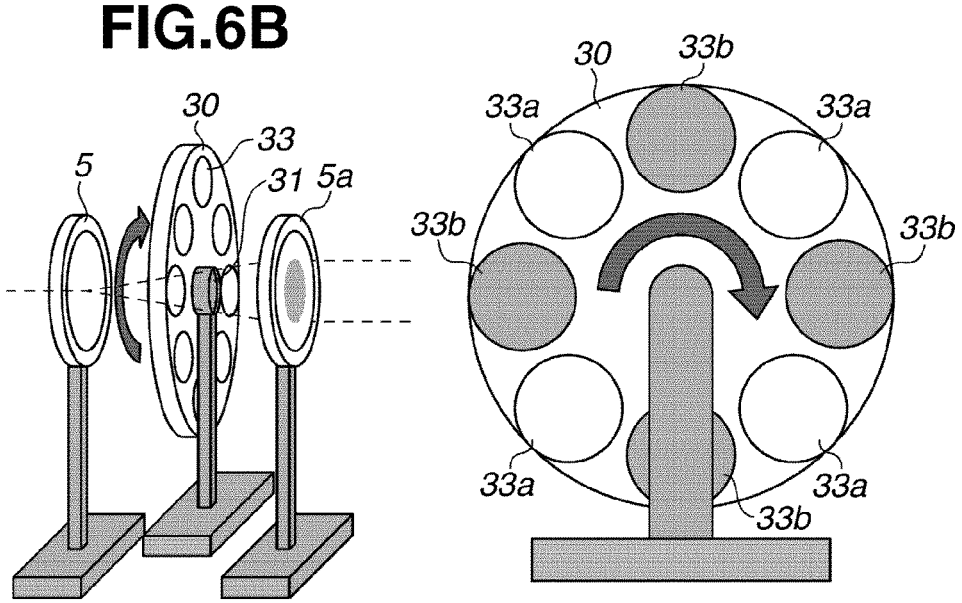

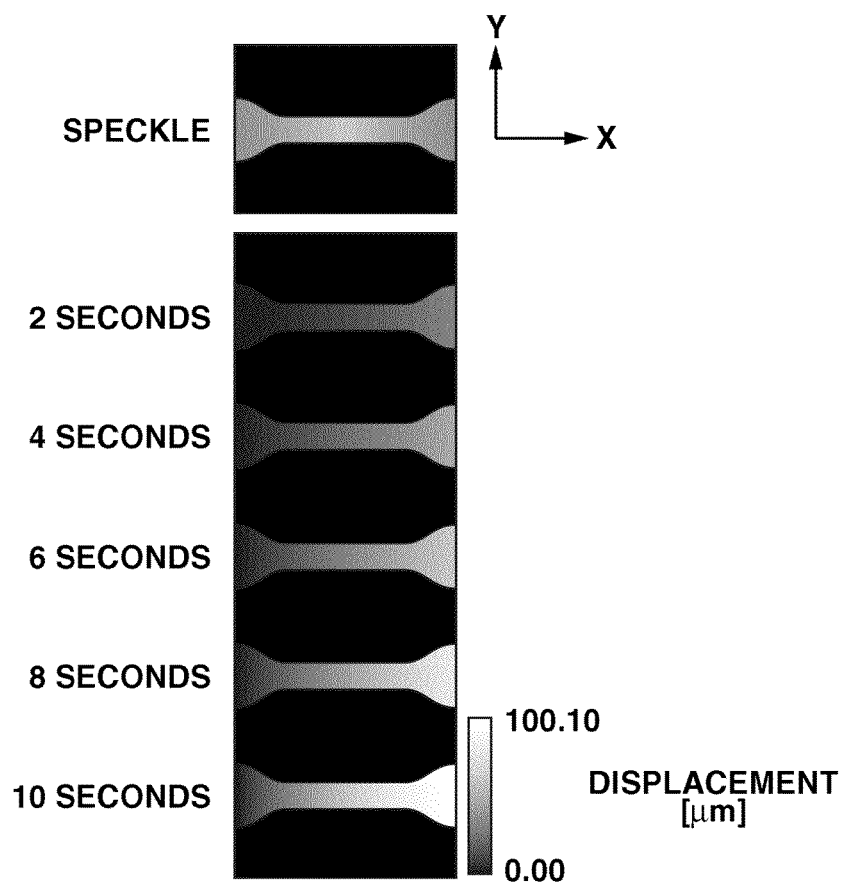

DEFORMATION MEASURING APPARATUS AND DEFORMATION MEASURING METHOD

BACKGROUND OF THE INVENTION

1. Field of the Invention

The present invention relates to a method for measuring an amount of deformation of an object, and more particularly, to a method for measuring, in a non-contact manner, the deformation of an industrial product caused by being pressed.

2. Description of the Related Art

A speckle interference method is an optical measuring method utilizing a spot-shaped bright and dark pattern (speckle interference pattern) generated when a rough-surfaced object is irradiated with a laser beam. Since the speckle interference pattern is an inherent pattern corresponding to a surface shape of an object to be measured which has been irradiated with a laser beam, the amount of deformation of the observed surface can be estimated from the change thereof.

First, two laser beams are irradiated on the object to be measured, and respective scattering lights generated on the observed surface of the measured object are caused to interfere with each other, and the bright and dark pattern (spot-shaped pattern corresponding to unevenness of the observed surface) is observed, thereby the speckle interference pattern can be obtained. In the speckle interference method, a highly accurate deformation measurement using a wavelength of light as a reference becomes possible.

FIG. 9 illustrates an example of an optical system used in the speckle interference method. A laser beam 1a emitted from a laser beam source 1 is divided into two laser beams by a beam splitter 2 which uses a half mirror or the like. Then, the respective laser beams are reflected by mirrors 3 and 4, and enlarged by the lenses 5 and 5a, and the lenses 6 and 6a, and the two laser beams are irradiated onto an object 7 to be measured.

The scattering lights from the object to be measured generate optical interference with each other, pass through a camera lens 8a, and an image is formed on an imaging surface of a camera 8. A speckle interference pattern acquired by the camera is input into a computer 9.

The speckle interference pattern is imaged again after a predetermined time length, and it is possible to measure what degree of deformation has been generated on the object 7 to be measured, by taking a difference from an original speckle interference pattern.

When the square of difference is calculated with respect to two speckle interference patterns before and after deformation of the object 7 to be measured, a fringe-shaped image (hereinafter, called a speckle interference fringe image) according to the amount of deformation is obtained. Then, the amount of deformation can be estimated from the number of fringes of the speckle interference fringe image. The relationship between the number of fringes and the amount of deformation has a relationship that as the amount of deformation becomes larger, the more fringes are generated.

The amount of deformation Δd per one fringe depends on a wavelength of laser, and an incident angle 10 into the object to be measured 7, and is expressed as equation (1) below, when incident angles of two laser beams are equal to each other, $$\Delta d = \frac{\lambda}{2\sin\theta} [nm] \quad (1)$$

where λ is wavelength of laser beam [nm], and θ is an incident angle [°].

However, as the amount of deformation becomes larger and the number of fringes increases, spatial frequencies of fringes which can be captured by the camera 8 have an upper limit, and thus the fringes are blurred to become unidentifiable. For this reason, the large deformation as the fringes are blurred cannot be measured.

Japanese Patent Application Laid-Open No. 6-94434 discusses a method for measuring a large deformation by temporally dividing and acquiring deformation of the object to be measured, and integrating the amounts of deformation. To describe in detail, when the speckle interference patterns are continuously acquired at the predetermined time intervals, difference between two continuous images is calculated from the acquired speckle interference patterns, and the amount of deformation is determined from the number of fringes. The final amount of deformation is determined by repetitively determining the amounts of deformation between the two speckle interference patterns, and summing them.

As described above, the technique discussed in Japanese Patent Application Laid-Open No. 6-94434 is to estimate the amount of deformation based on the number of fringes. As a minimum unit of the amount of deformation that is actually readable, about half of an amount of deformation of fringe (sub-micron order) is a limit, and as a reliable significant digit of measurement results (hereinafter, referred to as an accuracy), an order of micron becomes a limit.

SUMMARY OF THE INVENTION

According to an aspect of the present invention, a method for measuring, from an amount of phase change of an interference pattern generated by irradiating a object with a light, an amount of deformation of the object to be measured includes causing two laser beams to be incident on a object, detecting a first speckle interference pattern generated by an interference of scattering lights of the two laser beams, detecting a second speckle interference pattern generated by modulating an optical path length of at least one laser beam out of the two laser beams, and calculating an amount of deformation of the object by performing phase analysis on a speckle interference fringe image having a carrier fringe calculated based on difference between the first and the second speckle interference patterns.

According to another aspect of the present invention, an apparatus that measures, from an amount of phase change of interference pattern generated by irradiating a object to be measured with a light, an amount of deformation of the object, the apparatus includes a laser beam source, an optical system that guides two laser beams each from the laser beam source with respect to the object, a mechanism that modulates an optical path length of at least one out of the two laser beams, a detector that detects scattering light of the laser beam irradiated on the object, and a computer that calculates amounts of deformation based on speckle interference patterns detected by the detector. Amounts of deformation of the object are calculated, by performing phase analysis on a speckle interference fringe image having carrier fringes calculated based on a difference between a first speckle interference pattern generated by an interference of scattering lights of the two laser beams, and a second speckle interference pattern generated by the modulating the optical path length.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIGS. 3A and 3B are flowcharts of a deformation measuring method according to an exemplary embodiment of the present invention.

FIGS. 6A, 6B, and 6C each illustrate a plan view and feature portions of the measuring apparatus according to a second exemplary embodiment of the present invention.

FIG. 7 illustrates a result of experiment example according to an exemplary embodiment of the present invention.

DESCRIPTION OF THE EMBODIMENTS

Various exemplary embodiments, features, and aspects of the invention will be described in detail below with reference to the drawings.

Figure 1:
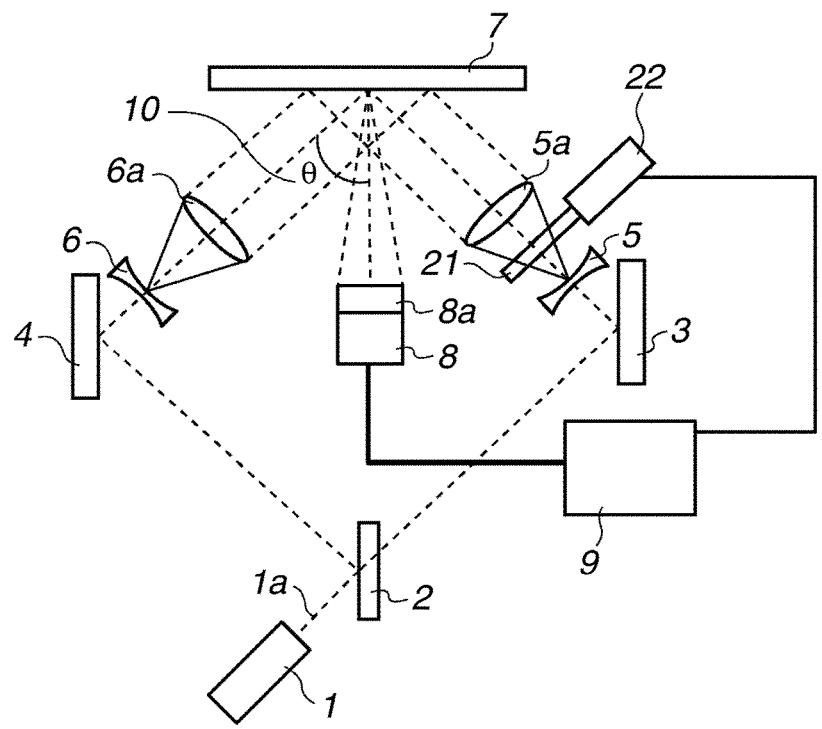
FIG. 1 is a plan view of a deformation measuring apparatus according to an exemplary embodiment of the present invention.

FIG. 1 illustrates a basic configuration of a deformation measuring apparatus according to an exemplary embodiment of the present invention. A laser beam 1a emitted from a laser beam source 1 is divided into two laser beams by a beam splitter 2.

One laser beam is reflected by a mirror 4, and thereafter is enlarged by a lens 6, to become a non-collimated light as drawn in FIG. 1. Then, the laser beam is collimated by a lens 6a and irradiated onto an object 7 to be measured.

Another laser beam is reflected by a mirror 3, and thereafter is similarly enlarged by a lens 5 to become a non-collimated light, and then passes through a plane parallel transparent plate 21. Then, the other laser beam is collimated by a lens 5a, and is irradiated onto the object 7 to be measured. The transparent plate 21 is used to exert a change to the optical path length of the laser beam.

As will be described below, in the present exemplary embodiment, a driving apparatus 22 and the plane parallel transparent plate 21 constitutes an optical path length modulating mechanism. The transparent plate 21 is driven and controlled by the driving apparatus 22, according to a driving signal from a computer 9.

The driving apparatus 22 has any one or more driving functions of placement of the plane parallel transparent plate 21 onto the optical path, or removal from the optical path, or tilt relative to an optical axis of the transparent plate 21, replacement with a transparent object with different refractive index or thickness.

By placing the plane parallel transparent plate 21 on the optical path of the diffused light, the laser beam will be irradiated at varying incident angles depending on a location of a light-projected surface of the transparent plate 21. When an incident angle of the laser beam into the plane parallel transparent plate is varied, a distance traveled by the laser beam through the transparent plate changes. By utilizing this principle, change of the optical path length can be caused.

Since the non-collimated light includes converged light, the present invention is not limited to diffused light. A configuration for placing the transparent plate on the optical path of the converged light may be used.

A scattering light from the object to be measured passes through a camera lens 8a, and is observed by the camera 8 serving as a detector. A speckle interference pattern generated by the scattering light captured by the camera (hereinafter, called a speckle interference pattern) is input into the computer 9.

Then, the amount of phase change is calculated and accordingly the amount of deformation of the object to be measured is calculated, based on the speckle interference patterns each detected at a certain time, and at subsequent specific time points, by the computer 9.

Figure 2C:
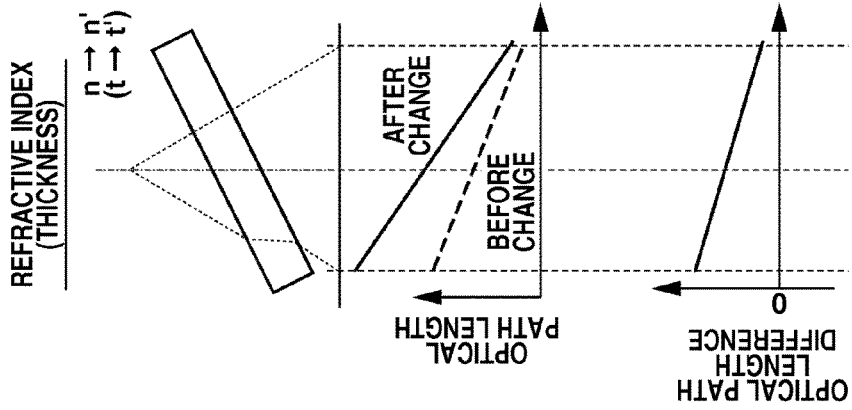
FIGS. 2A, 2B, and 2C illustrate a formation method of optical path length difference distribution according to an exemplary embodiment of the present invention.
Figure 2B:
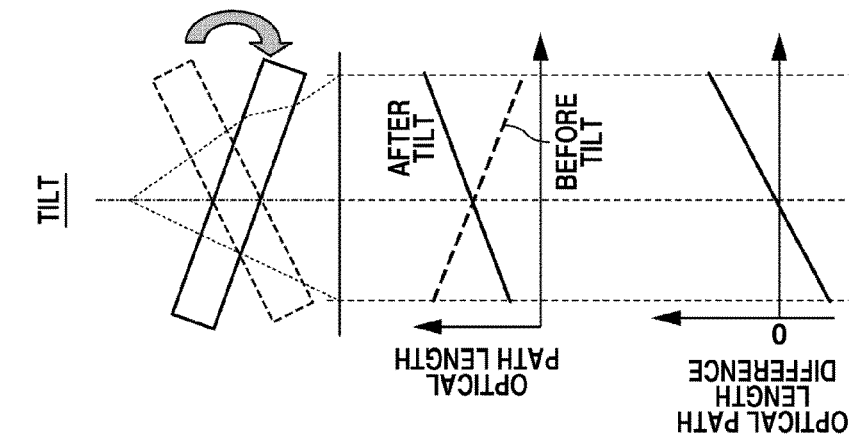
Figure 2A:
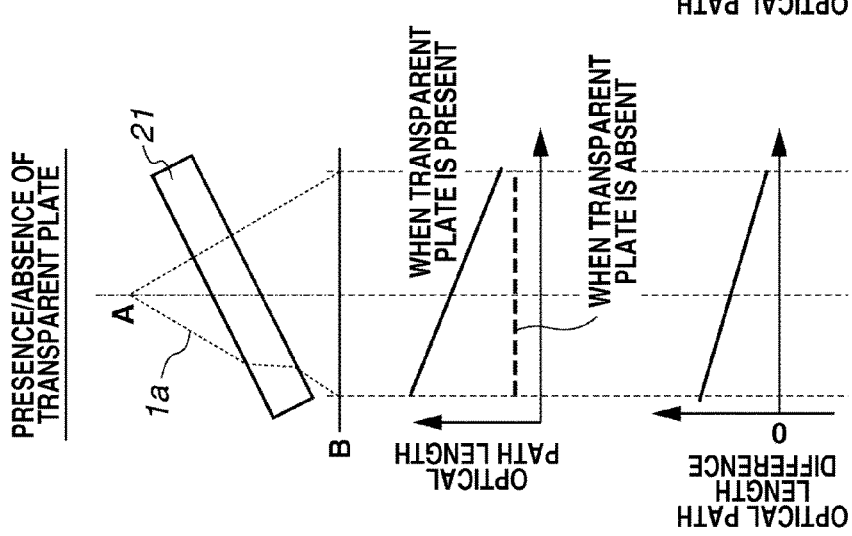

FIGS. 2A, 2B, and 2C illustrate that a difference in the optical path length between the optical paths arises, according to positions at which the laser beams pass through the transparent plate, out of the laser beams that pass through the transparent plate, depending on arrangements of the transparent plate. FIGS. 2A, 2B, and 2C illustrate path lengths and optical path length differences depending on presence or absence of the transparent plate tilted and arranged with respect to the laser beam, depending on a tilt angle, and depending on change of refractive index or thickness of the transparent plate tilted and arranged with respect to the laser beam, respectively.

It is found that the optical path length can be modulated, and distribution can be formed in the optical path length difference by changing a state (presence or absence, tilt angle, refractive index, thickness) of the transparent plate. "Optical path length difference" indicates a difference which arises between the optical path lengths of respective optical paths, depending on presence or absence of the transparent plate, or before and after tilting thereof.

In the present exemplary embodiment, the optical path length is modulated, at the formation of carrier fringes described below. Monotonous change in the optical path length difference is described below on FIG. 2.

The above-described optical path length distribution is configured such that, when the transparent plate is absent, the optical path length from a point "A" to a surface "B" becomes uniform as illustrated by a dashed line in a middle graph in FIG. 2A. FIG. 2C illustrates the optical path length, and the optical path length difference, when n>n', t>t', but refractive index and thickness may become smaller.

Next, measurement procedure according to the present exemplary embodiment will be described with reference to a flowchart illustrated in FIG. 3A.

In step F1, the speckle interference pattern is acquired.

In step F2, either one of processes is performed from placement and removal of the plane parallel transparent plate to and from the optical path that becomes a non-collimated light, and change in the tilt angle and replacement with a transparent plate with different refractive index, and thickness, if the transparent plate has been placed in advance. Through the above-described process, modulation can be given on the optical path length before and after the processing to one laser beam out of two laser beams, thereby distribution can be formed in the optical path length difference.

The processes in step F1 for acquiring a plurality of speckle interference patterns at specific time intervals, and in step F2 for creating distribution on the optical path length difference obtained by giving modulation on the optical path length are alternately performed until the measurement is completed. Thereafter, in step F3, the measurement ends.

In step F4, the square of the difference two continuous speckle interference patterns is calculated, out of the obtained speckle interference patterns, and an speckle interference fringe image is acquired. In this speckle interference fringe image, the fringe called a carrier fringe is detected as an image superposed on the speckle interference fringe image by the modulation of the above-described optical path length.

Hereinbelow, an example for acquiring the speckle interference fringe image by calculating the square of the difference between the speckle interference patterns will be described, but as a matter of course, an absolute value of the difference may be used, or another calculation method may be utilized.

The Phases of fringes of the speckle interference fringe image having the carrier fringes are acquired. A derivation of the phases will be performed among all the speckle interference patterns that are temporally continuous, and if N frames of the speckle interference patterns have been acquired, then N−1 frames of phases will be obtained.

For example, if three frames of the speckle interference patterns is acquired, two phases between the first and the second frames, and between the second and the third frames are acquired. Then, a total amount of deformations of the object to be measured is determined as the sum of the amounts of deformation obtained from the two phases.

If there is distribution of the optical path length difference between the two speckle interference patterns acquired at adjacent time points, carrier fringes are generated. As a result, binary values representing two states such as removal and placement of the transparent plate, or reverse of the tilt of the transparent plate may be alternately used.

A conversion from the phases of the speckle interference fringes into amounts of deformation of the object to be measured is executed based on the Equation 1 representing an amount of deformation Δd per one speckle interference fringe.

From the wavelength of the laser beam to be used or incident angle relative to the object to be measured, or the like, a relationship between the phase of speckle interference fringe image and amount of deformation is to be determined in advance and used.

The above-described derivation of the phase of the speckle interference fringe uses a publicly known spatial Fourier transformation method, or a spatial Hilbert transformation method as a phase analysis method for the interference fringe.

In order to use the phase analysis method by the publicly know spatial Fourier transformation method, or the spatial Hilbert transformation method, a carrier fringe with a spatially high-frequency is superposed on a speckle interference fringe image to be analyzed. For this reason, in order to superpose the carrier fringe on the speckle interference fringe image, an optical path length difference distribution is formed in one laser beam out of two laser beams, between an interval of acquisition of two images.

A procedure for the spatial Fourier transformation method will be described. A speckle interference fringe image on which a carrier fringe is formed, is expressed by the following equation (2), $$I_{(x,y)} = I_0[1 + r\cos\{\psi_{(x,y)} + 2\pi f_0 x\}] \quad (2)$$

where, r is visibility of the interference fringe, $\psi_{(x,y)}$ is a phase of speckle interference fringe image corresponding to the deformation of the object to be measured, $2\pi f_0 x$ is the phase of carrier fringe, and $f_0$ is a known spatial frequency of carrier fringe.

First, a speckle interference fringe image expressed by the equation (2) is Fourier transformed in the X direction, and if $f_0$ is sufficiently large, terms in which $f_0$ is dominant can be separated. Here, when inverse Fourier transformation is performed on the term, the following equation (3) is obtained.

$$I_{f_0(x,y)} = I_0 r \exp[i\{\psi_{(x,y)} + 2\pi f_0 x\}] \quad (3)$$

Since the equation (3) is expressed by complex amplitude, the phase of a speckle interference fringe on which a carrier fringe is formed, is obtained from arctangent of the ratio of the imaginary part to the real part like the following Equation (4).

$$\psi_{(x,y)} + 2\pi f_0 x = \arctan\left(\frac{\mathrm{Im}(I_{r(x,y)})}{\mathrm{Re}(I_{r(x,y)})}\right)[\mathrm{rad}] \quad (4)$$

The spatial Hilbert transformation method uses the characteristic of the Hilbert transformation method by which the signal shifted from the original signal by 90 degrees can be obtained. First, as expressed by equation (5), the average intensity is subtracted from the speckle interference image expressed by equation (2).

$$I_{(x,y)} - I_0 = I_0 r \cos\{\phi_{(x,y)} + 2\pi f_0 x\} \quad (5)$$

When the Hilbert transformation is performed in the X direction on the equation (5) as a cosine wave, and the equation (5) and an arctangent of the ratio are determined, a phase of the speckle interference fringe on which a carrier fringe is formed, is obtained as equation (6).

$$\psi_{(x,y)} + 2\pi f_0 x = \arctan\left(\frac{G_{(x,y)}}{I_{(x,y)}}\right)[\mathrm{rad}] \quad (6)$$

Since the arctangent is used for the phase analysis, the phase is calculated in a convoluted state within a range from −π to π. For this reason, a phase jumping occurs at intervals of 2π, even in a case where the phase is continuous. The phase jumped positions are determined, and the phase value of 2π is added (or subtracted) each time the phase jump occurs, so as to correct the phase jumping, whereby correct phase information can be obtained. The above-described phase correction is known as a phase unwrapping.

Subsequently, in step F5, the phase convoluted within the range from −π to π obtained in step F4 is corrected to correct phase information by the phase unwrapping. The phase information obtained in step F5 is information on which a phase corresponding to a component of a carrier fringe is superposed, and includes error component irrelevant to deformation information to be obtained.

In step F6, a phase (second term of left-hand side in equation (6)) corresponding to a carrier fringe component which results in an error is removed. The phase corresponding to the carrier fringe component is determined by calculation from the optical path length difference distribution, after the distribution of the optical path length differences has been determined in advance from change amounts of the refractive index, thickness, incident angle, and tilt angle of the transparent plate. Further, while the object to be measured is standing still (ψ(x, y)=0), the phase corresponding to the carrier fringe component may be obtained empirically.

However, in step F4, when the spatial Fourier transformation method is used, the carrier fringe component can be cancelled. In this case, the processing in step F6 can be omitted. A procedure for performing cancellation is to extract a high-frequency component by a filter in a Fourier region, and subsequently to return only a frequency moved by the carrier fringe to a low-frequency side (in other words, second term of right-hand side in the equation (3) is extracted to be $J_{1(f,y)}$).

Then, the phase of the speckle interference fringe image excluding the carrier fringe component can be determined, by performing inverse Fourier transformation on this signal, and determining an arctangent of the ratio of the imaginary part to the real part.

In step F7, first, the obtained phase information is integrated. Then, the integrated phase information is converted into the amount of deformation, from the relationship between the phase of the speckle interference fringe image and amount of deformation. The relationship between the phase of speckle interference fringe and the amount of deformation may be calculated from the wavelength, incident angle into the object to be measured, using the equation (1), and the amount of deformation is determined from the following conversion equation.

$$\Delta d_{(x,y)} = \frac{\lambda}{4\pi \sin\theta} \psi_{(x,y)} [nm] \qquad (7)$$

In a case of integrating pieces of deformation information, $\Psi_{(x,y)}$ in the equation (9) may be replaced by $\Sigma\Psi_{(x,y)}$. In addition, in order to perform dynamic measurement, it becomes possible to evaluate deformation process with respect to time change by increasing or decreasing the number of pieces of phase information which is integrated from the start of measurement.

Through the above steps, a publicly-known phase analysis method can be also applied to the speckle interference measurement method by using the carrier fringe. More specifically, the phase of the speckle interference fringe image can be obtained, and a minimum unit of readable displacement amount can be fined compared with conventional technique that counts the number of fringes. As a result, a highly accurate measurement becomes possible.

Further, another measurement method in the present invention will be described with reference to the flowchart in FIG. 3B. Although FIG. 3B is similar to FIG. 3A, steps F2A and F8, which are different steps from the steps of FIG. 3A, will be described.

In step F2A, it is characterized by causing a method for changing the optical path length difference distribution to have repetitive periodicity.

More specifically, if placement and removal of the transparent plate, which is arranged tilted relative to the laser beam, are performed, the placement and removal are alternately performed using one type of the transparent plate. In addition, when the tilt angle of the transparent plate is changed, the transparent plate is tilted in an opposite direction for each acquisition of the speckle interference patterns by a certain tilt angle.

Alternatively, when replacing with a transparent plate with different refractive index and thickness, two types of transparent plates are alternately used. Whichever method may be used, since distribution of the optical path length differences occurs in temporally adjacent speckle interference patterns, a carrier fringe is generated on the speckle interference fringe image.

By placement and removal, or change of the tilt angle of the above-described transparent plate, it becomes possible to give a distribution of the optical path lengths different from the distribution of the optical path lengths given right before.

Figure 4A:
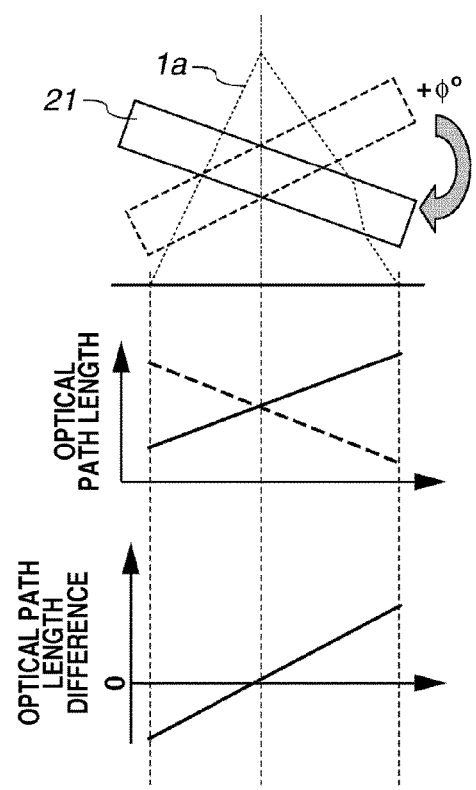
FIGS. 4A and 4B illustrate optical path length difference distribution of inverse gradient according an exemplary embodiment of to the present invention.
Figure 4B:
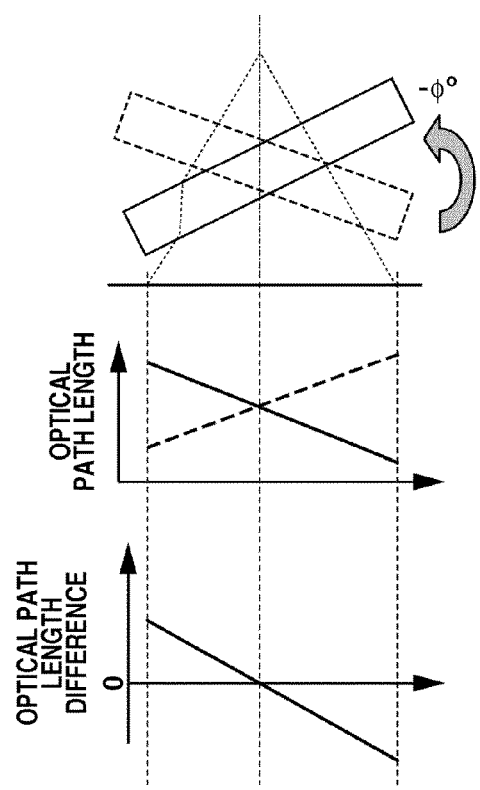

Here, an example of changing the tilt angle of the transparent parallel plate will be described. FIGS. 4A and 4B illustrate changes of the optical path length distributions, when the tilt angle of the transparent plate 21 is set at a fixed amount $\phi$, and the transparent plate 21 is tilted in opposite directions to each other by the tilt angle ($\phi$).

When the tilt angle is changed from $+\phi$ to $-\phi$, or changed from $-\phi$ to $+\phi$, distribution can be given on the optical path length differences before and after tilt. In this case, the distribution of the optical path length differences becomes an inverse gradient. (i.e., $2\pi f_0 x$ at right-hand side in equation (2) can be turned to $-2\pi f_0 x$).

The optical path length difference distribution using the above-described transparent plate is given each time the speckle interference pattern is acquired. Through the processing in step F2A of the flowchart, temporally adjacent deformation information, out of continuous deformation information obtained from the speckle interference pattern, becomes the one on which a carrier fringe component formed by the optical path length difference distribution of each inverse gradient is superposed.

In step F8, the amount of deformation is determined by summing phase information on which the carrier fringe component is superposed for each even number of pieces of the phase information. Since the carrier fringes formed by the optical path length difference distribution of each inverse gradient are superposed on continuous and adjacent phase information, the carrier fringe components can be cancelled by summing respective pieces of phase information.

Through the processing in step F8, removal of the carrier fringe component, or removal within the Fourier transformation method is not necessary in step F6 in FIG. 3A, calculation error and measurement error associated with the carrier fringe removal are not superposed. As a result, more accurate deformation measurement becomes possible.

Figure 5:
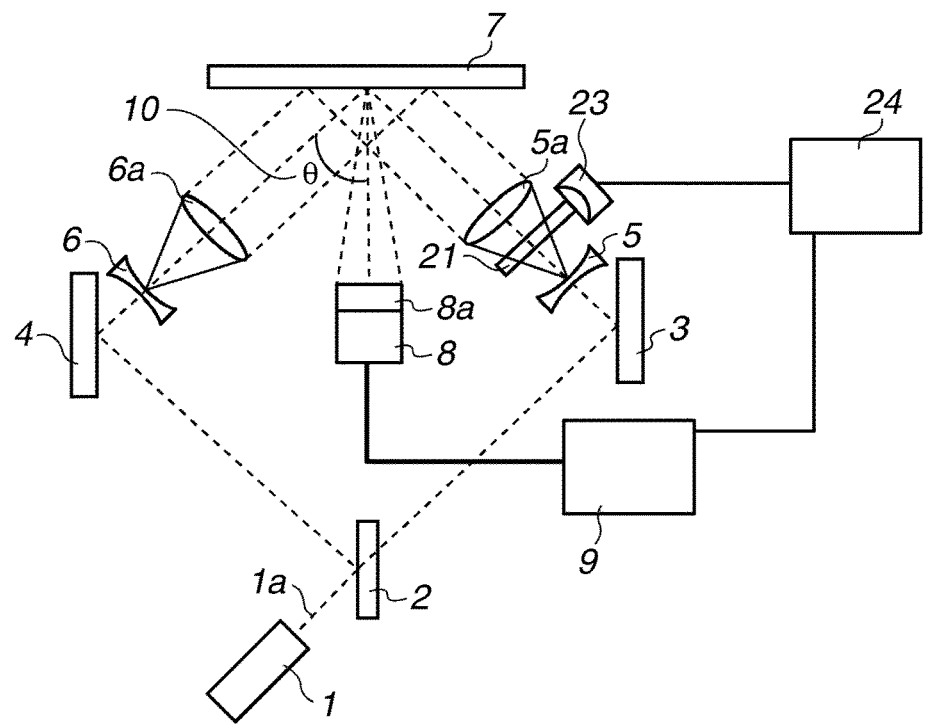
FIG. 5 is a plan view of the measuring apparatus according to a first exemplary embodiment of the present invention.

In the deformation measuring apparatus according to the present invention, an exemplary embodiment for tilting the transparent plate relative to the optical path so as to superpose the carrier fringe on the speckle interference pattern will be described with reference to FIG. 5.

The laser beam source 1 uses He—Ne laser (wavelength: 632.8 nm), and the laser beam is enlarged up to Φ150 mm by the lenses 5 and 5a, and the lenses 6 and 6a. Synthetic silica (Φ50 mm, thickness 1 mm) is used for the plane parallel transparent plate, and the above-described synthetic silica is placed between the lenses 5 and 5a.

A gonio-stage 23 is used for a tilt drive. A stage controller 24 for controlling the gonio-stage 23 from a computer 9 is equipped. A camera lens 8a uses a lens with f=75 mm, F4, and a camera 8 uses a charge-coupled device (CCD) camera having a number of pixels of 1600×1200.

The computer 9 has a central processing unit (CPU) with an operation frequency of 2.33 GHz, and a memory of 2 GByte.

A driving condition of the gonio-stage is to enable repetitive formation of the carrier fringes to be performed by tilting the transparent plate in opposite directions every time the speckle interference pattern is acquired. The tilt angle varies depending on an irradiation range of laser, a field of view of the camera, the number of pixels, and the diameter of a laser beam passing through the transparent plate.

If there are too many carrier fringes, the fringes are blurred to become unidentifiable, and accordingly the carrier fringes forming at a tilt angle at which about 30 carrier fringes are generated, in the number of pixels of the camera according to the present exemplary embodiment.

In the present exemplary embodiment, the irradiation range of the laser is φ180 mm, the field of view of the camera is 150 mm×112 mm, and the laser diameter when passing through the transparent plate is 5 mm, and a tilt angle is set to 15°.

By alternately performing acquisition of the speckle interference pattern and the tilt, the carrier fringes can be superposed on the speckle interference fringe image. As a result, it has become possible to measure large deformation of the object to be measured with a high accuracy.

In a deformation measuring apparatus according to the present invention, an exemplary embodiment when a refractive index of the transparent plate is changed, will be described with reference to FIGS. 6A to 6C. FIG. 6A is a plan view of the apparatus configuration. Neodymium doped yttrium lithium fluoride (Nd:YLF) laser is used for the laser beam source 1, and an electron multiplying charge coupled device (EM-CCD) camera is used for the camera 8. The number of pixels of the EM-CCD camera is 1024×1024. A second exemplary embodiment has similar configuration to that in the first exemplary embodiment except for the laser beam source 1 and the camera 8, and the driving apparatus that forms the optical path length difference distribution.

FIGS. 6B and 6C schematically illustrate the driving apparatus for forming the optical path length difference distribution. As illustrated in FIG. 6B, the driving apparatus for forming the optical path length difference distribution includes a holder 30 having a plurality of windows 33 in a revolver-like manner, a motor 31 for rotating and driving the holder 30, and a motor control driver 32. The plurality of windows 33 can contain the transparent plate.

An optical sapphire and a synthetic silica each having thickness of 2 mm serving as two types of the transparent plates with different refractive indexes, are placed at windows 33a and 33b illustrated in FIG. 6C, such that the tilt angles become equally 45° relative to the optical axis when a light wave passes through the window.

The above-described holder 30, as illustrated in FIG. 6A, is arranged so that a radially diffused laser beam (non-collimated light) passes through one of the windows of the holder 30. Then, the holder 30 is rotated by the motor 31, and imaging timing of the camera and timing at which the laser beam passes through the window 33 are synchronously controlled. By performing the control, it becomes possible to generate the optical path length difference distribution between different windows.

However, as the holder 30 is rotated at a higher speed, it becomes possible to perform deformation measurement of the object to be measured at a shorter time interval, but an exposure time becomes shorter. For this reason, a high-output laser, or a high-sensitivity camera is used.

In the above-described exemplary embodiment, the transparent plates with different refractive indexes are used, but the transparent plates may be arranged at the windows 33a and 33b so that at least one or more conditions are different from each other, out of a refractive index, a thickness, and a tilt angle. Alternatively, the transparent plate may be arranged only in either one of the window 33a and window 33b, and the transparent plate may not be arranged in the other window.

With the above-described configuration, the object to be measured can be measured with a high accuracy.

EXPERIMENTAL EXAMPLE

Using the apparatus according to the first exemplary embodiment, the amount of deformation is measured by subjecting a metal piece processed to a shape of dumbbell test specimen to stretched deformation by a tensile testing machine.

Figure 8:
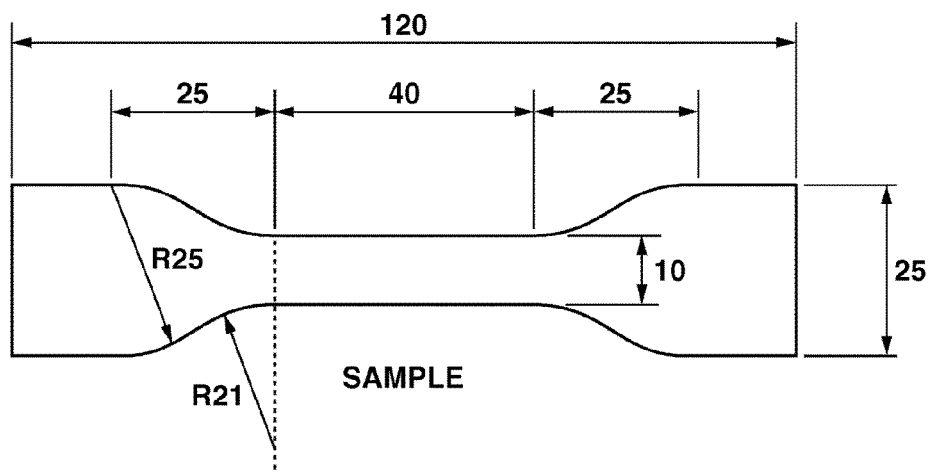
FIG. 8 illustrates a shape of a sample used in the exemplary embodiment of the present invention.
Figure 9:
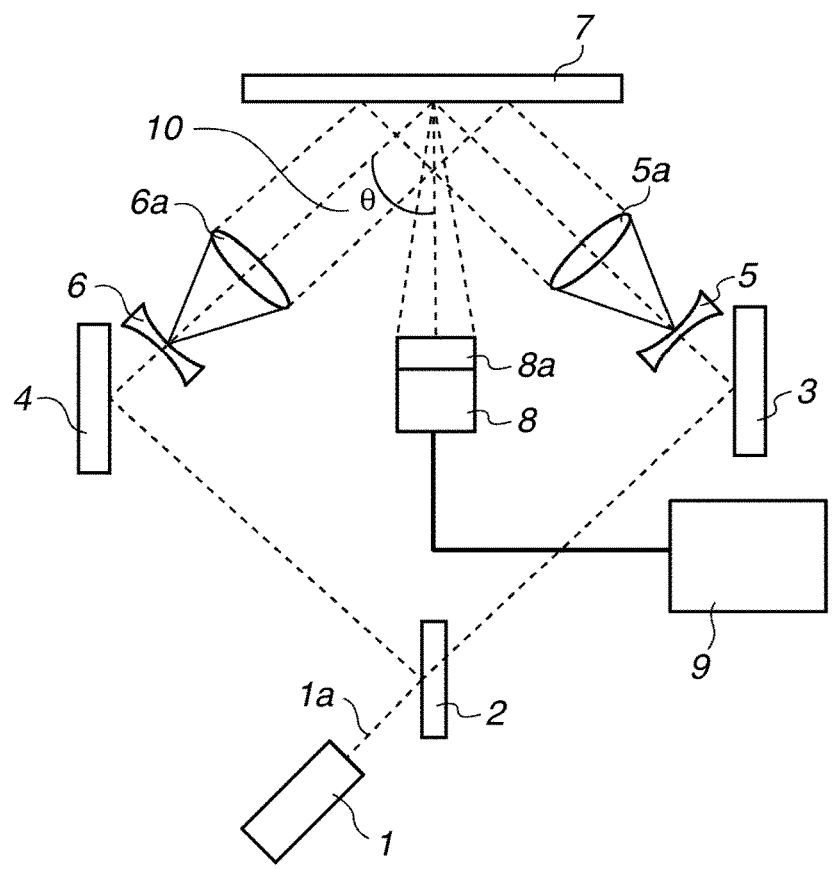
FIG. 9 is a plan view illustrating an example of a deformation measuring apparatus by the speckle interference method.

As a sample, a plate made of SUS304 with the thickness of 0.01 mm which has been processed to a shape of No. 1 dumbbell (JIS standards) (see FIG. 8). The above-described sample was attached on the tensile testing machine, and the speckle interference patterns were acquired at intervals of 0.5 sec, while pulling the sample at a tensile speed of 10 μm/s.

The sample was placed so that the incident angles of two laser beams into the sample each become 45° and −45° from the normal line, within a plane composed of an axis parallel to pulling direction and passing through a center of the sample, and the normal line of the center of the sample.

The tilt angle of the gonio-stage is set to 5°, and the sample was repetitively tilted in opposite directions, every time the speckle interference pattern was acquired, and measurement was terminated 10 seconds after the start of pulling (pulled about 100 μm).

FIG. 7 illustrates a result of the deformation amount of the sample which was measured by the deformation measuring method according to the present exemplary embodiment. The tensile test was performed by fixing the sample at left-end, and pulling it toward right-hand (x direction). Further, amounts of tensile displacement were measured using a heterodyne laser displacement gage.

Using the spatial Fourier transformation method, 20 pieces of the phase information were determined from the obtained 21 speckle interference patterns. The acquired pieces of phase information were integrated under a total five sets of conditions of 2 sec, 4 sec, 6 sec, 8 sec, and 10 sec from the start of measurement, and were converted into pieces of deformation information using the equation (1) from the laser wavelengths and the incident angles.

FIG. 7 illustrates speckle interference patterns during measurement and the result of deformation states which were measured at intervals of 2 sec from the start of pulling. As illustrated in FIG. 7, it can be seen that amount of displacement increase from left to right.

When the square of the difference between the speckle interference patterns before and after pulling is calculated, and a fringe image is determined, it was impossible to determine the amount of deformation since the fringes were blurred due to large deformation.

While the amount of displacement after 10 sec measured by the heterodyne laser displacement gage is 100.13 μm, the amount of displacement at right end of measurement result in the present invention was 100.10 μm. From the fact that a good agreement with the heterodyne laser displacement gage is obtained, it indicated that the large deformation of the order of 100 μm can be measured with a precision of sub-micron order.

The amount of deformation per one fringe is the order of 0.45 μm from the equation (1), and even a readable minimum amount of deformation is reduced by half, that is, the order of 0.225 μm. For this reason, the precision of conventional technique becomes micron order. For this reason, it indicates that measurement can be carried out with about one-digit higher precision by the present technique.

As illustrated in the present experimental example described above, it indicates that deformation in a direction along a measured surface generated by pulling or the like of the object to be measured can be measured with a high accuracy.

The present invention can be suitably utilized for the deformation measuring apparatus that measures deformation generated by pressing industrial products in a non-contact manner.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-129275 filed Jun. 4, 2010, which is hereby incorporated by reference herein in its entirety.

What is claimed is:

1. A method for measuring, from an amount of phase change of an interference pattern generated by irradiating an object to be measured with light, an amount of deformation of the object, the method comprising:

causing two laser beams to be incident on the object;

detecting a first speckle interference pattern generated by an interference of scattering lights of the two laser beams;

detecting a second speckle interference pattern generated by modulating an optical path length of at least one laser beam out of the two laser beams;

obtaining a speckle interference fringe image having a carrier fringe calculated based on difference between the first and the second speckle interference patterns;

obtaining a phase of the speckle interference fringe image including a phase corresponding to the deformation of the object and a phase of a spatial carrier fringe;

unwrapping the phase of the speckle interference fringe image; and calculating an amount of deformation of the object based on phase information corrected by the phase unwrapping, wherein a method for the modulating an optical path length of the laser beam includes causing a plane parallel transparent plate, arranged on an optical path where either one of the two laser beams becomes diverging light and at a position where the plane parallel transparent plate transmits said either one of the two laser beams, to tilt relative to the optical path.

2. The method according to claim 1, further comprising:

calculating the amount of deformation by performing phase analysis on each of the speckle interference fringe images, having carrier fringes obtained from the two speckle interference patterns at adjacent time points when detected, out of three or more speckle interference patterns detected by modulating the phase of the laser beam, and by summing a plurality of the amounts of deformation.

3. The method according to claim 1, wherein a method for performing the phase analysis is a spatial Fourier transformation method or a spatial Hilbert transformation method.

4. An apparatus that measures, from an amount of phase change of interference pattern generated by irradiating an object to be measured with light, an amount of deformation of the object, the apparatus comprising:

a laser beam source;

an optical system configured to guide two laser beams each from the laser beam source to the object;

a mechanism configured to modulate an optical path length of at least one of the two laser beams;

a detector configured to detect scattering light of a laser beam irradiated on the object; and a computer configured to calculate an amount of deformation based on speckle interference patterns detected by the detector, wherein the amount of deformation of the object is calculated, by:

obtaining a speckle interference fringe image having a carrier fringe calculated based on difference between the first and the second speckle interference patterns, obtaining a phase of the speckle interference fringe image including a phase corresponding to the deformation of the object and a phase of a spatial carrier fringe, unwrapping the phase of the speckle interference fringe image, and calculating an amount of deformation of the object based on phase information corrected by the phase unwrapping, wherein the mechanism is a mechanism for causing a plane parallel transparent plate, arranged on an optical path where either one of the two laser beams becomes a diverging light and at a position where the plane parallel transparent plate transmits said either one of the two laser beams, to tilt relative to the optical path.

5. The apparatus according to claim 4, wherein the computer calculates the amount of deformation by performing phase analysis on each of the speckle interference fringe images, having carrier fringes obtained from the two speckle interference patterns at adjacent time points when detected, out of three or more speckle interference patterns detected by modulating the phase of the laser beam, and by summing a plurality of the amounts of deformation.

6. The apparatus according to claim 4, wherein the performing the phase analysis uses a spatial Fourier transformation or a spatial Hilbert transformation.

* * * * *